United States Patent
Mc Ie et al.

(10) Patent No.: US 6,786,897 B2
(45) Date of Patent: Sep. 7, 2004

(54) TEMPERATURE INDICATOR AND INSULATOR FOR POWERED SURGICAL INSTRUMENTS

(75) Inventors: John M. Mc Ie, New Port Richey, FL (US); Glenn A. Tatjes, Palm Harbor, FL (US)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 09/931,619

(22) Filed: Aug. 16, 2001

(65) Prior Publication Data

US 2003/0036747 A1 Feb. 20, 2003

(51) Int. Cl.$^7$ ............................................. A61B 17/00
(52) U.S. Cl. ........................... 606/1; 374/141; 374/162
(58) Field of Search ............................... 606/1, 31, 24, 606/167, 170; 374/141, 162; 607/102

(56) References Cited

U.S. PATENT DOCUMENTS

| | | | | |
|---|---|---|---|---|
| 3,651,695 A | * | 3/1972 | Brown | 374/147 |
| 3,827,301 A | * | 8/1974 | Parker | 374/162 |
| 4,028,118 A | * | 6/1977 | Nakasuji et al. | 106/31.19 |
| 4,325,254 A | * | 4/1982 | Svacina et al. | 607/114 |
| 5,496,342 A | * | 3/1996 | Urich | 374/162 |
| 5,899,569 A | * | 5/1999 | Favale | 374/141 |
| 5,934,181 A | * | 8/1999 | Adamczewski | 374/141 |
| 6,005,484 A | * | 12/1999 | Ko | 374/162 |
| 6,245,096 B1 | * | 6/2001 | Tomic-Edgar et al. | 607/107 |
| 2002/0097778 A1 | * | 7/2002 | Moroskat et al. | 374/162 |

* cited by examiner

Primary Examiner—Roy D. Gibson
Assistant Examiner—Jocelyn Ram
(74) Attorney, Agent, or Firm—Gene Warzecha

(57) ABSTRACT

A temperature sensing device for attachment to a powered surgical instrument operating a workpiece such as a bur. The device is a thermochromic element which may be embodied as a paint or a thermal insulating device. The device embodiment is in the form of a thermoplastic, elastomeric material which changes color at a predetermined temperature and is formed in a shape adapted to enable the device to be affixed to the distal end of the instrument, adjacent the collet connecting the workpiece to the instrument. The device is attached in a contiguous manner so frictional heat generated by moving parts of the instrument may be conducted through contiguous surfaces of the instrument and the device. The thermochromic element provides a visual indication of the temperature of a portion of the instrument when the temperature exceeds a predetermined level.

35 Claims, 4 Drawing Sheets

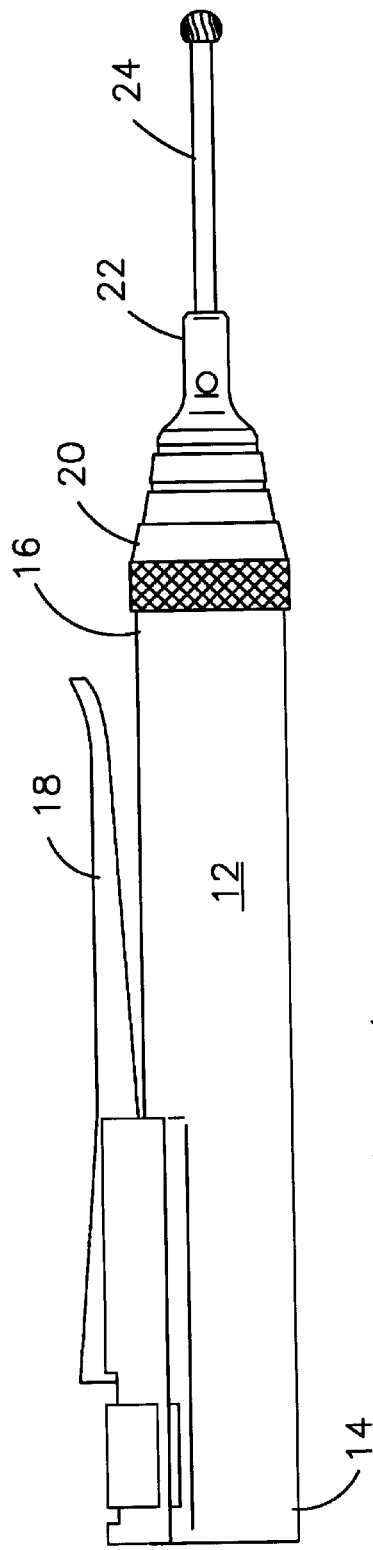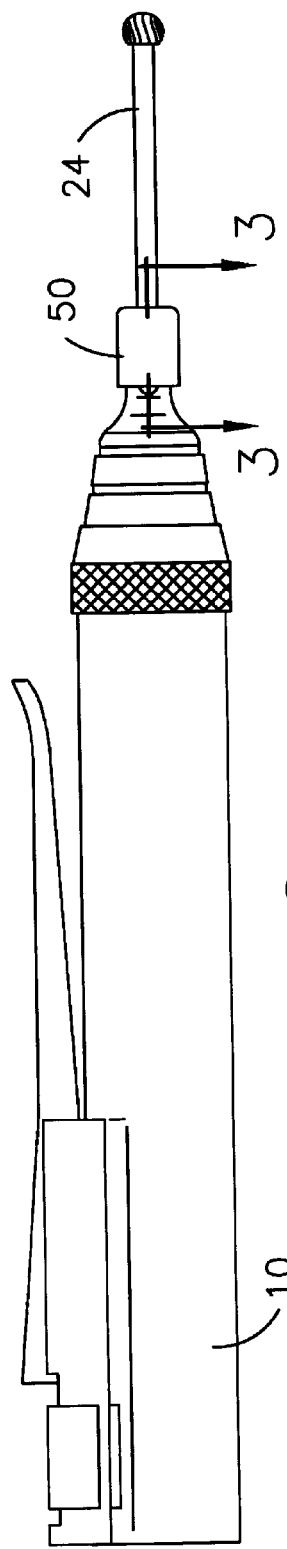
Fig. 1
PRIOR ART
Fig. 2

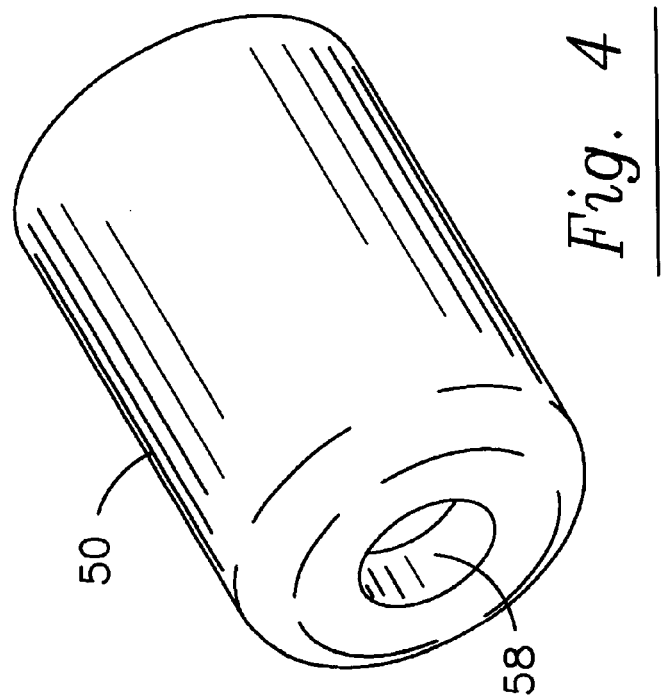
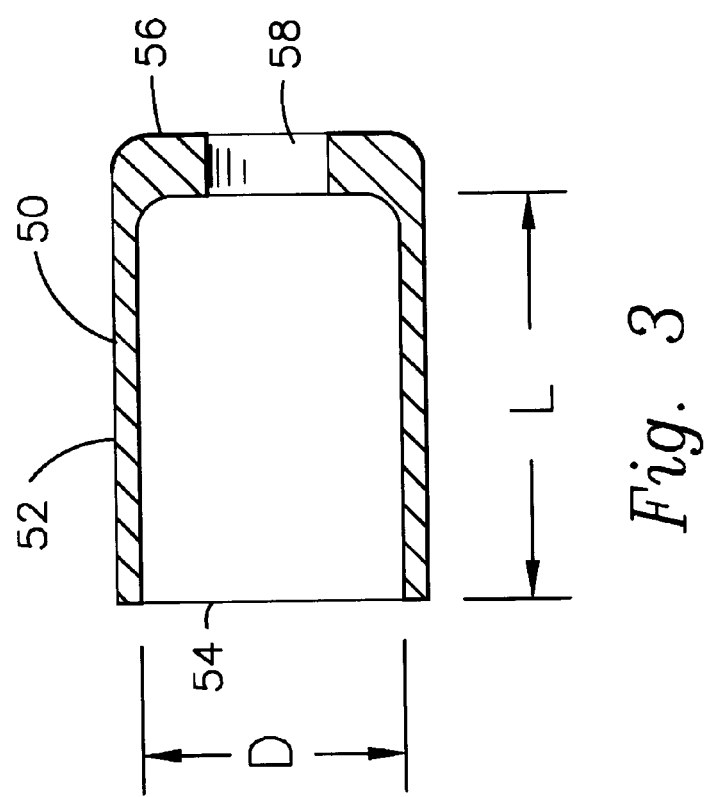

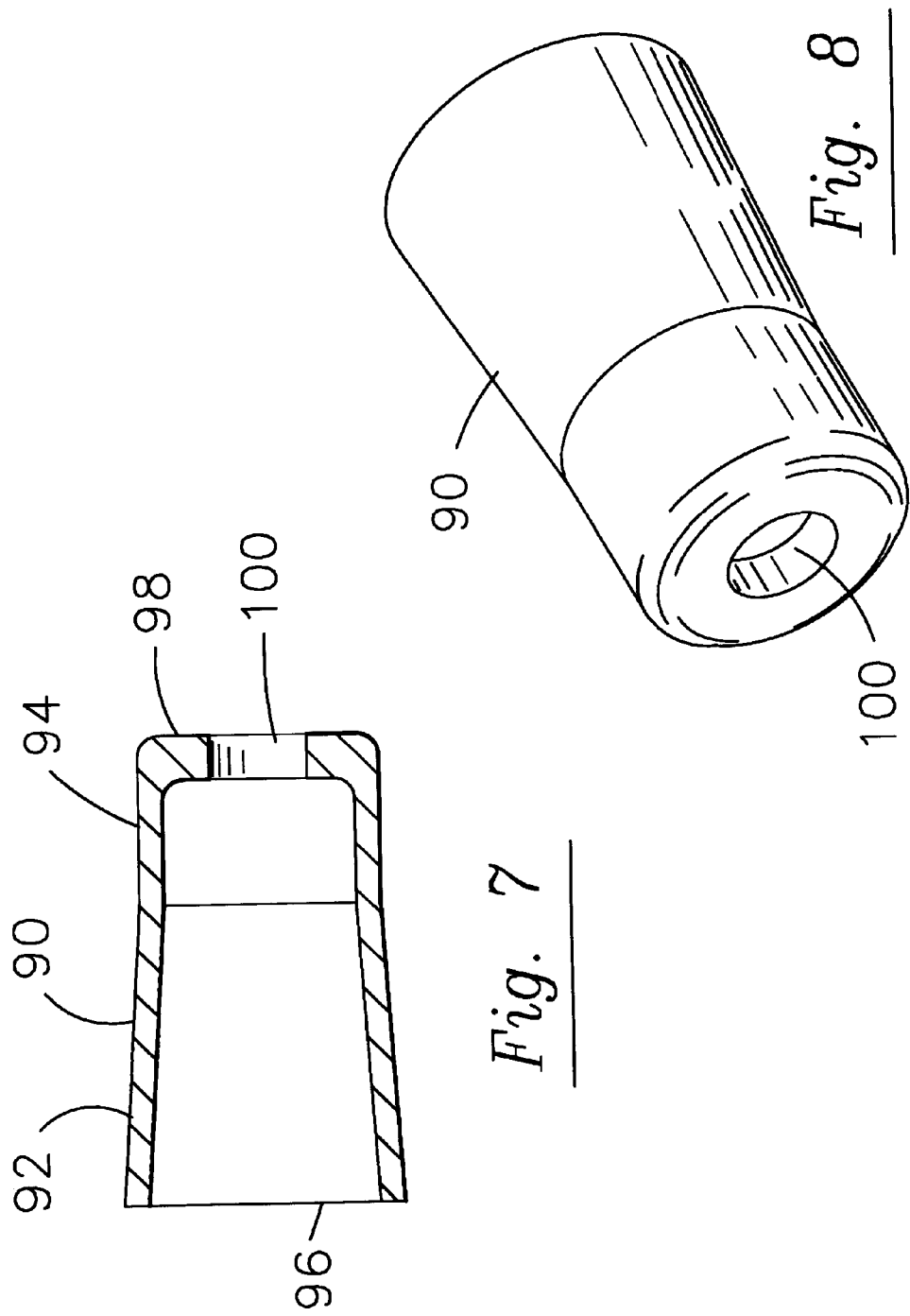

TEMPERATURE INDICATOR AND INSULATOR FOR POWERED SURGICAL INSTRUMENTS

BACKGROUND OF THE INVENTION

1. Field of the Invention

The invention relates to powered surgical instruments. More particularly, the invention relates to temperature indicating elements for use with powered surgical instruments to provide a visual indication of the temperature of at least a portion of the surgical instrument. The invention also relates to thermal insulating devices for use with powered surgical instruments, these devices optionally including temperature indicating elements.

2. Description of the Prior Art

Powered surgical instruments are known for use during surgical procedures to operate a workpiece in some manner to perform the procedure. For example, a powered surgical instrument may be a handpiece, generally powered either electrically or pneumatically, in the form of a drill which rotates a drill bit or bur. Other handpiece instruments in the form of a saw operate a saw blade in either a reciprocating or oscillating manner. Various other types of powered surgical handpieces are known to move a tool or workpiece in various ways to perform surgical procedures.

In some powered surgical instruments the workpiece (e.g. burr or drill bit, etc.) is rapidly rotated to, for example, debride or resect soft tissue or bone. The workpiece is locked into a collet at the distal end of the instrument for fixed attachment to the motor drive shaft in the instrument. The workpiece generally extends distally from the collet in alignment with the axis of the drive shaft. In some instances a bur guard or similar bearing-containing device is interposed between the workpiece and the handpiece in order to provide additional rotary bearing support between the workpiece and the handpiece. In all instances, the rapid movement of the workpiece relative to the stationary components of the handpiece creates heat-generated friction which ultimately passes via thermal conduction or radiation from the internal friction-generating components to the external surface of the handpiece or bur guard (or other component). The invention is described in terms of powered surgical instruments because manually operated instruments would not be expected to generate a great deal of frictional heat. Clearly, if a manual instrument did generate sufficient heat to cause concern, the invention would be equally applicable to such instruments.

While powered surgical instruments are designed to be cleaned and sterilized after each use, it has been found that less than optimal cleaning and/or sterilization by users contributes to greater than normal generation of friction upon subsequent use and, consequently, greater than normal temperature rise in the components of the instrument and/or workpiece. In some instances, the heat generated by a powered surgical instrument may be so great as to make it unable to be held by a surgeon or may be so great as to cause injury to a patient. In particular, use of such potentially very hot instruments in small areas, such as during oral surgical procedures, raises the possibility that a patient will be burned inadvertently. It would, therefore, be desirable to provide some indication that a part of the surgical instrument is beginning to get hotter than intended. It would also be desirable to provide a way to protect the patient from sudden temperature increases of surfaces of powered surgical instruments likely to come in contact with the patient.

It is accordingly an object of this invention to produce a temperature indicating device to provide an indication of the temperature of at least a portion of a powered surgical instrument.

It is another object of this invention to provide a temperature indicating device for attachment to a specific portion of a powered surgical instrument to provide a visual indication of the temperature of that portion.

It is also an object of this invention to provide a temperature indicating device for attachment at the distal end of a powered surgical instrument adjacent to the collet through which the workpiece passes.

It is yet another object of this invention to provide a temperature indicating device capable of attachment to the distal end of an instrument at a location most clearly visible by a user.

It is an additional object of this invention to produce a method for indicating a predetermined temperature of a portion of a surgical instrument.

It is still another object of this invention to provide a thermal insulator device to be interposed between a patient and a potentially high temperature portion of a powered surgical instrument being used on the patient.

It is also an object of this invention to provide such a thermal insulating device with a temperature indicating element to provide a visual indication of the temperature of the portion of the powered surgical instrument to which it is attached.

SUMMARY OF THE INVENTION

These and other objects of the invention are achieved by the preferred embodiment disclosed herein which is a thermochromic indicating device for providing a visual signal indicative of a temperature change of at least a portion of a powered surgical instrument. The instrument has a proximal end and a distal end, the distal end being generally cylindrical and adapted to have an elongated workpiece extending distally therefrom. The indicating device is a generally cylindrical shell having an open proximal end and a closed, apertured distal end, a cylindrical wall with an axis and a predetermined axial length. The end wall enclosing the distal end has a workpiece-receiving aperture. The cylindrical wall is adapted to be received in contiguous engagement on the distal end of the instrument with the workpiece extending through said workpiece-receiving aperture. A temperature sensitive dye is embedded in the cylindrical shell to sense the temperature of the distal end of the instrument which is in contiguous engagement with the cylindrical shell. The dye changes color at a predetermined temperature to provide a visual indication of a change in the temperature of the device.

Another aspect of the invention is a device such as that described above, but without any thermochromic elements therein. Such a device would have insulating properties alone.

Another aspect of the invention is a thermochromic element embodied in the form of a paint having thermochromic elements therein. Such an embodiment would not necessarily have the insulating properties of the previous embodiments.

Another aspect of the invention is the method of operating a powered surgical instrument with the insulating and/or thermochromic elements described above. These methods comprise the steps of affixing the insulating and/or thermochromic elements to a selected portion of a powered surgical instrument as it is being used on a patient.

BRIEF DESCRIPTION OF THE DRAWINGS

FIG. 1 is a side elevational view of a powered surgical instrument.

FIG. 2 is a side elevational view of the instrument of FIG. 1 having attached thereto a temperature indicating device constructed in accordance with the principles of this invention.

FIG. 3 is a cross-sectional view of the temperature indicating device of the invention taken along the lines 3—3 of FIG. 2.

FIG. 4 is a front perspective view of FIG. 3.

FIG. 7 is a cross-sectional view of FIG. 6 taken along the line 7—7.

FIG. 8 is a front perspective view of FIG. 7.

DESCRIPTION OF THE PREFERRED EMBODIMENT

Figure 5:
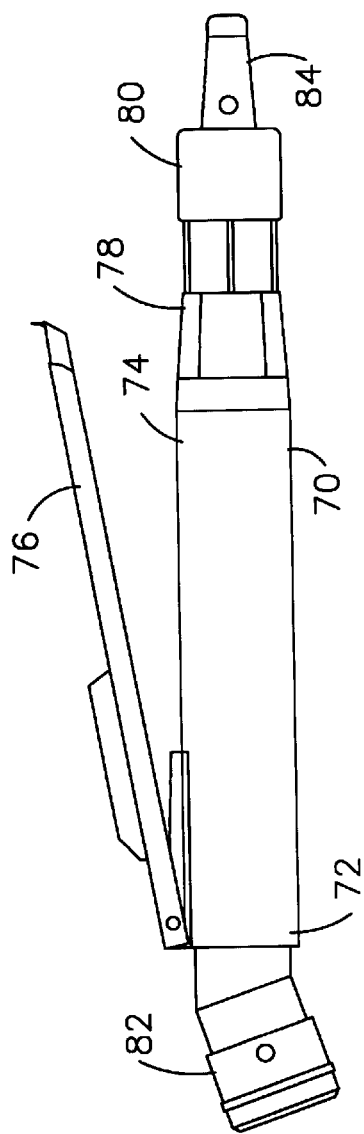
FIG. 5 is a side elevational view of an alternate powered surgical instrument.

An example of a powered surgical instrument 10 is shown in FIG. 1. Instrument 10 includes a body 12 having a proximal end 14, a distal end 16 and an operating on/off lever/switch. Proximal end 14 is attachable via an electrical connection (not shown) to which an electrical power cable (not shown) may be attached. Distal end 16 is provided with a collet mechanism 20 and a bearing-containing bur guard 22. Workpiece 24, shown in the form of a bur, is rotatably secured to the output shaft of a drive motor within body 12. The shaft of workpiece 24 passes through bur guard 22 and collet 20 into engagement with the drive shaft (not shown). Collet 20 serves to rotatably lock workpiece 24 adjacent the drive shaft while bur guard 22 contains rotary bearings which provide additional support (especially for long burs) to maintain the axis of workpiece 24 in alignment with the axis of the output drive shaft of the motor within body 12. The configuration shown in FIG. 1 is one prior art example of a surgical handpiece in combination with a workpiece.

FIG. 2 shows the handpiece 10 of FIG. 1 assembled with a thermally insulating and temperature indicating element such as device 50 best seen in FIGS. 3 and 4. It will be understood that device 50 could be made without temperature indicating elements in which case it would have insulating properties only. Device 50 is made in the form of a cylindrical shell 52 having an open proximal end 54 and a closed distal end wall 56. The inner diameter D (which may be slightly undersized to create a good fit on the bur guard) and inner length L of shell 50 are sized to fit on the corresponding distal portion of bur guard 22. Aperture 58 in end wall 56 is sized to permit the shaft of workpiece 24 to pass therethrough without any contact. Device 50 thus is fixedly secured to, and in contiguous engagement with bur guard 22 while not impeding the movement of workpiece 24.

Device 50 is shaped to mate with a selected portion of the particular surgical instrument for which it is designed. If one desires to use a device such as device 50 on a different surgical instrument, or on a different portion of an instrument, the device just needs to be shaped accordingly to fit where intended. It would also be possible to attach a thermally insulating and temperature indicating device in any shape (flat, curved, etc.) with an auxiliary attachment mechanism (not shown) such as a screw or adhesive. The advantage of the cylindrical shape of the preferred embodiment is that it is functional and visible over a 360° range around the instrument.

In the preferred embodiment, device 50 is integrally molded of an elastomeric material enabling it to be secured to the distal end of bur guard 22 with a simple friction fit ensuring contiguous engagement between the inner cylindrical surface of device 50 and the outer cylindrical surface of bur guard 22. Contiguity facilitates good thermal conductivity between contiguous surfaces which in turn facilitate reliable temperature indication. It will be understood there is also contiguous contact between the end wall 56 and the corresponding end portion of bur guard 22 (not shown). In the preferred embodiment, device 50 is approximately 0.4 inches in length, with L=0.35 inches, D=0.222 inches, the thickness of wall 52 equal to 0.005 inches and the diameter of aperture 58 equal to 0.1 inches.

The polymeric material from which device 50 is formed is, in the preferred embodiment, a polypropylene compound which, if temperature indicating properties are desired, additionally contains a conventional thermochromic dye which changes color depending upon the temperature of the device. The material is a mixture of a first polypropylene material containing a red dye which is not notably temperature sensitive and a second polypropylene material containing a blue dye which is temperature sensitive. While many different thermochromic dyes are known and available in many colors and temperature ranges, the preferred embodiment utilizes a microencapsulated leuco dye which changes from a color to clear at the selected temperature. As the temperature of the blend of first and second polypropylene material changes, the resultant color of the blend, which is normally purple at room temperature changes (in varying degrees, depending upon temperature) to bright pink or red. Since the color change visually indicates an undesirable temperature increase which indicates some unintended, friction-generating element in the instrument, any color change should be interpreted as an indicator signaling that the instrument should not be used until it has been repaired. The polymeric material from which device 50 is made is a proprietary thermoplastic resin compound Colorcomp® M-1000, color # BL5-778-1 TCH available from LNP Engineering Plastics, Inc., 251 South Bailey Road, Thorndale, Pa. The temperature range at which the color changes may be varied, depending upon the proprietary formulation of the colorant in the polypropylene, although in the preferred embodiment the selected temperature range is from approximately 135° F., at which point the color change begins to occur, to approximately 150° F., at which point a full color change could be expected. Leuco dyes are not extremely precise in the temperature at which they change color, but because the invention is intended as a gross indicator of heat, precision is not essential. It should be noted that while the color change may occur at the aforementioned temperatures, the insulation properties of the material mitigate the potential for patient burns because of its poor heat transferability (i.e. specific heat value). Additionally, the color of the material of the device varies in a gradient through a cross-section causing color changes before the outside surface of the device reaches the same temperature as the internal surface.

While the thermochromic material is, in the preferred embodiment, embedded in device 50, it will be understood that thermochromic material could simply be mixed with a paint or similar medium to be painted on the device or otherwise topically applied or associated with the device (the term "associated" is used to mean the thermochromic material could be on or in the device). It could even be made to read "HOT" or other words at a given temperature.

Figure 6:
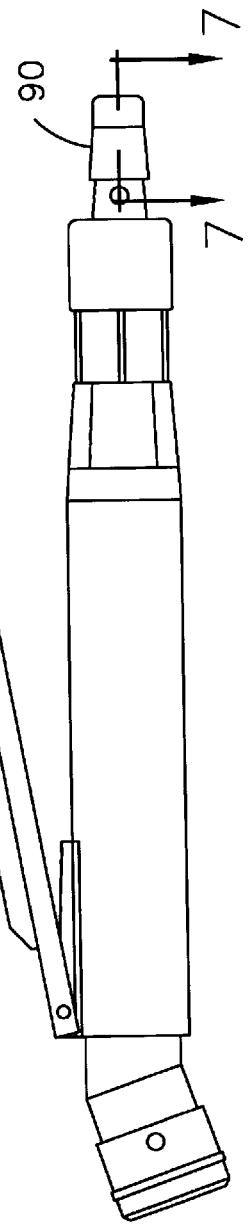
FIG. 6 is a side elevational view of the powered surgical instrument of FIG. 5 having a temperature indicating device attached thereto.

It will be understood that device 50 may be made disposable and may be made in a variety of shapes and sizes in order to enable it to be secured to a variety of powered surgical instruments and at a variety of locations on a given powered surgical instrument. For example, another prior art powered surgical instrument is shown in FIG. 5 as instrument 70 having a proximal end 72 and a distal end 74. Instrument 70 has an on/off lever/switch 76, a collet mechanism 78 and a bur guard 80. Instrument 70 is operated pneumatically and has a pneumatic connection 82 adjacent proximal end 72 although, while it will be noted that bur guard 80 has a frustoconical distal tip 84, in all other respects the general operation of instrument 70 is similar to that instrument 10 in that instrument 70 also rotates a workpiece (not shown). Because of the frustoconical shape of the distal tip of bur guard 80, a thermoplastic device 90, best seen in FIGS. 6, 7 and 8 must have a corresponding frustoconical internal shape. Thus, device 90 has a frustoconical wall 92 adjacent a cylindrical wall 94 and sections 92 and 94 are bounded by open ends 96 and closed end wall 98, respectively. End wall 98 contains a workpiece-receiving aperture 100. In all other respects the operation of temperature device 90 is similar to that of temperature indicating device 50.

While the temperature indicating embodiments of the invention have been described in terms of a thermochromic element to be applied via a paint medium or a device such as a shell adapted to contiguously fit a cylindrical bur guard, it will be understood that the temperature indicating element may be attached to the powered surgical instrument at any desired location which may be a potential heat source or where a temperature indication is desired. For example, if a particular instrument has two components which are movable relative to each other so that friction generated heat may be produced and transferred by conduction or radiation from one component to the other, a temperature indicating element could be used. In this circumstance the element could be in the form of a device attached in contiguous relationship (using techniques described above or any suitable attachment mechanism) to a place on the instrument adjacent, but not necessarily contiguous to the source of heat. Indeed, the source of heat need not be frictional, and it will be understood that any heat source (chemical, thermal radiation, etc.) serving to produce potentially detrimental effects may be monitored by a temperature indicating element as described above. The monitoring may even be accomplished with the indicating element spaced away from the heat source, provided that heat is ultimately transferred by some means to the device in order to activate the thermochromic material.

It will be understood by those skilled in the art that numerous improvements and modifications may be made to the preferred embodiment of the invention described herein without departing from the spirit and scope thereof.

What is claimed is:

1. An indicating device for providing a visual signal indicative of a temperature change of at least a portion of a powered surgical instrument, said instrument having a generally cylindrical portion adapted to have a workpiece extending distally therefrom, said device comprising:
    a generally cylindrical shell comprising:
        a cylindrical wall having a proximal end and a distal end, an axis and a predetermined axial length,
        an end wall enclosing said distal end, and
        a workpiece-receiving aperture in said end wall;
    said cylindrical wall adapted to be received in contiguous engagement on said cylindrical portion of said instrument with said workpiece extending through said workpiece-receiving aperture; and
    temperature sensitive means for sensing the temperature of said cylindrical portion of said instrument in contiguous engagement with said cylindrical shell and for providing a visual indication of a predetermined temperature of said cylindrical portion.

2. An indicating device according to claim 1 wherein said generally cylindrical shell is integrally formed from an elastomeric material.

3. An indicating device according to claim 2 wherein said temperature sensitive means comprises material embedded within said generally cylindrical shell.

4. An indicating device according to claim 3 wherein said temperature sensitive means comprises a thermochromic dye.

5. An indicating device according to claim 1 wherein said temperature sensitive means exhibits said visual indication when said predetermined temperature is within a range of approximately 135° F. to 150° F.

6. An indicating device according to claim 1 wherein said cylindrical wall comprises a first portion adjacent said end wall, said first portion being cylindrical, and a second portion adjacent said first portion, said second portion being frustoconical.

7. The indicating device of claim 1 wherein said shell comprises a thermally insulating material.

8. In combination, a powered surgical instrument and a temperature indicating device, said powered surgical instrument comprising:
    a first component and a second component;
    a source of heat associated with one of said first or second components, said heat being transferred to the other of said first or second components;
    said temperature indicating device comprising an element adapted to be affixed to said powered surgical instrument, adjacent one of said first or second components in order to sense the temperature thereof, said temperature indicating device adapted to provide a visual indication of a predetermined change in temperature thereof.

9. The combination of claim 8 wherein said temperature indicating device comprises a material conforming in shape to that portion of said powered surgical instrument to which it is affixed.

10. The combination of claim 9 wherein said temperature indicating device is a paint comprising thermochromic elements.

11. The combination of claim 9 wherein said temperature indicating device is a polymeric material.

12. An indicating device for use with a surgical instrument having a potential heat generating surface adjacent a tissue contacting portion of said surgical instrument, said device comprising:
    a body having a conforming surface similar in shape to said heat generating surface, said conforming surface attachable adjacent said heat generating surface; and
    thermochromic means associated with said body and having a first color at a first temperature of said body and a second color at a second temperature of said body.

13. An indicating device according to claim 12 wherein said conforming surface is cylindrical.

14. An indicating device according to claim 12 wherein said thermochromic means is a leuco dye.

15. An indicating device according to claim 14 wherein said leuco dye is within said body and wherein said body is molded.

16. The indicating device of claim 12 wherein said body comprises a thermally insulating material.

17. An indicating device for use with a surgical instrument having a potential heat generating surface, said device comprising:
   a body having a conforming surface similar in shape to said heat generating surface, said conforming surface attachable adjacent said heat generating surface; and
   thermochromic means associated with said body and having a first color at a first temperature of said body and a second color at a second temperature of said body,
   wherein said body is a cylindrical shell having an open proximal end and a closed, apertured distal end.

18. A method for operating a surgical instrument comprising the steps of:
   identifying a first portion of a surgical instrument, adjacent a second, tissue contacting portion of said surgical instrument, which may be heated to a predetermined temperature;
   applying to said first portion a temperature indicating element which can sense the temperature of said first portion and provide an indication that said first portion is at a predetermined temperature;
   sensing the temperature of said first portion with said temperature indicating element;
   providing an indication that said first portion is at said predetermined temperature.

19. A method according to claim 18 wherein said step of providing comprises providing a visual indication.

20. A method according to claim 19 wherein said visual indication is a color change of said temperature indicating element.

21. A method for operating a surgical instrument comprising the steps of:
   identifying a surface of a surgical instrument which may become a potential heat generating surface, said surface being adjacent a tissue contacting portion of said surgical instrument;
   providing an indicating device comprising:
      an element having a conforming surface similar in shape to said heat generating surface, said conforming surface attachable to said instrument adjacent said heat generating surface; and
      thermochromic means associated with said element and having a first color at a first temperature of said element and a second color at a second temperature of said element;
   attaching said element to said surgical instrument with said conforming surface adapted to receive heat from said heat generating surface;
   sensing heat with said thermochromic means;
   noting the color change of said thermochromic means at said second temperature.

22. A method according to claim 21 wherein said element is a body preformed to have said conforming surface.

23. A method according to claim 21 wherein said element is paint comprising said thermochromic means.

24. The method of claim 21 wherein said element having a conforming surface comprises an insulating material and further comprising the step of interposing said insulating material between said surface of said surgical instrument and surrounding patient tissues.

25. In combination, a powered surgical instrument and temperature indicating device, said powered surgical instrument comprising:
   a first component and a second component;
   a source of heat associated with one of said first or second components, said heat being transferred to the other of said first or second components, said source of heat being frictional, said heat caused by said first component being movable relative to said second component whereby frictional heat may be conducted between said first and second components;
   said temperature indicating device comprising an element adapted to be affixed to said powered surgical instrument, adjacent a portion of one of said first or second components in order to sense the temperature thereof, said temperature indicating device adapted to provide a visual indication of a predetermined change in temperature thereof.

26. The combination of claim 25 wherein said temperature indicating device comprises a body having a conforming surface conforming in shape to that portion of said powered surgical instrument to which it is affixed.

27. The combination of claim 26 wherein said temperature indicating device is a paint comprising a thermochromic element.

28. The combination of claim 27 wherein said thermochromic element is a leuco dye.

29. The combination of claim 26 wherein said temperature indicating device is a polymeric material comprising a thermochromic element.

30. The combination of claim 29 wherein said body is molded and the thermochromic element comprises a leuco dye.

31. The combination of claim 29 wherein said body is a cylindrical shell having an open proximal end and a closed, apertured distal end.

32. An indicating device according to claim 26 wherein said conforming surface is cylindrical.

33. The combination of claim 25 wherein said temperature indicating device comprises a thermally insulating material.

34. The combination of claim 33 wherein said thermally insulating material will be interposed between said portion and surrounding patient tissues.

35. The combination of claim 34 wherein said temperature indicating device is a polymeric material comprising a thermochromic element.

* * * * *